US005971971A

United States Patent [19]

Saint-Ramon et al.

[11] Patent Number: 5,971,971

[45] Date of Patent: Oct. 26, 1999

[54] POUCH FOR PACKAGING BIOLOGIC LIQUID SUBSTANCES WITH PEELABLE OPENING FOR INSERTION OF CANNULAE, TUBES AND PROBES

[75] Inventors: Jean-Gérard Saint-Ramon, Montmorency; Claude Dassier, Fontaine la Guyon; Christian Beau, Voisins-le-Bretonneux; Francis Lesieur, L'Aigle, all of France

[73] Assignee: Instruments de Medicine Veterinaire, France

[21] Appl. No.: 08/884,005

[22] Filed: Jun. 27, 1997

[30] Foreign Application Priority Data

Jun. 28, 1996 [FR] France .................................. 96 08095

[51] Int. Cl.[6] .................................................... A61B 19/00

[52] U.S. Cl. ............................................................ 604/408

[58] Field of Search .................................... 604/408, 409, 604/410, 411, 412, 413, 416

[56] References Cited

U.S. PATENT DOCUMENTS

| | | | |
|---|---|---|---|
| 4,198,972 | 4/1980 | Herb | 604/408 |
| 4,365,629 | 12/1982 | Pert et al. | 604/408 |
| 4,439,192 | 3/1984 | Leurink | 604/408 |
| 4,465,487 | 8/1984 | Nakamura et al. | 604/408 |
| 5,176,634 | 1/1993 | Smith et al. | 604/87 |
| 5,251,982 | 10/1993 | Lennart A. et al. | 604/408 |
| 5,364,384 | 11/1994 | Grabenkort et al. | 604/408 |
| 5,391,163 | 2/1995 | Christine et al. | 604/408 |

*Primary Examiner*—John G. Weiss
*Assistant Examiner*—Ki Yong O
*Attorney, Agent, or Firm*—Morgan & Finnegan, L.L.P.

[57] ABSTRACT

A pouch or sachet for packaging biologic liquid substances is made of two thermoplastics material films welded together. The weld delimits a pocket. A filler passage is connected to the top of the pocket. One of the thermoplastics material films has a peelable area at the top. The peelable area contains wax. After filling, the pouch is sealed in a sealing area inside the peelable area, near the top of the passage and transversely to its axis. The pouch can be opened easily, in the required area, without using any cutting tools, by manually separating the two thermoplastics material films. Positive guidance is then assured on insertion of a probe into the passage of the pouch.

11 Claims, 3 Drawing Sheets

POUCH FOR PACKAGING BIOLOGIC LIQUID SUBSTANCES WITH PEELABLE OPENING FOR INSERTION OF CANNULAE, TUBES AND PROBES

BACKGROUND OF THE INVENTION

1. Field of the Invention

The present invention concerns a pouch or sachet for packaging biologic liquid substances. In particular, the invention concerns a pouch for packaging biologic liquid substances in the field of human medicine, for example blood, liquid medications, vaccines or urine, or in the veterinary field, for example animal semen or any other biological liquid for artificial insemination of animals, blood, liquid medications, vaccines or urine etc.

By way of illustration, the present invention will first be described with reference to the veterinary field, for packaging animal semen or any other biological liquid for artificial insemination.

2. Description of the Prior Art

This type of pouch, also known as a single dose pouch, is well known in the art and is the subject matter of FR-B-2 667 504 and EP-A-718 191. Provided that they are opened correctly, the pouches described in these references allow fast volumetric filling, protected from air and contamination, secure and sealed coupling of the pouch and the tube or probe before insemination, and natural complete draining of the pouch, protected from the air and from contamination. It is often difficult to open the pouches, however, which causes problems when they are used.

When using this type of pouch, which includes a filler passage, usually extended by an insertion and centering cone and through which its contents can be recovered or drained, an opening is made in the pouch at the location of said passage and the free end of a probe or a tube is inserted into this opening.

There are currently two techniques for opening a ouch of this kind.

The first is the incision technique which is used in the case of a pouch with no precutting. In this case it is necessary to use a cutting or incision tool such as scissors or a stylet. This technique has the following disadvantages:

- it necessitates the use of a cutting tool,
- it requires the cutting tool to be cleaned each time a pouch is opened to preserve the sterility and freedom from contamination of the contents,
- it involves the risk of injury to the user,
- it requires complicated manipulation,
- it is difficult or even impossible to insert the probe or the tube if the cut is not made correctly.

In the case of a pouch with precutting, the packaging machine must be provided with a blade or a tool for precutting the film to provide a place for tearing to start. This technique, which necessitates the presence of a precutting station on the machine and regular replacement of the precutting blade or tool, has the following disadvantages:

- the precutting is associated with tearability of the thermoplastic material film constituting the pouch,
- consistent tearability cannot be achieved, which makes inserting the probe or the tube for recovering or draining the content difficult if not impossible.

The present invention solves these problems and provides a pouch for packaging liquids that can be opened simply and reliably, without using any tool or other object. Other aims and advantages of the invention will appear from the following description.

SUMMARY OF THE INVENTION

The present invention provides a pouch comprising two thermoplastics material films welded together by a weld delimiting a pocket and a filler passage connected to the top of the pocket wherein at least one of said two thermoplastic material films has a peelable area at the top of the pocket.

In a preferred embodiment, the peelable area includes a sealing and peelable material, for example wax. The sealing and peelable material can be deposited during the manufacture of the thermoplastics material sheet. The skilled person will understand that the sealing and peelable material must be inert in relation to the liquid to be packaged in the pouch.

In a preferred embodiment, the two thermoplastics material films have a vertical offset relative to each other at the top of the pocket, of about 2 mm to 3 mm, for example.

The pouches can be made and filled in a manner that is known in itself, for example using a machine of the type described in FR-B-2 667 504 or EP-A-718 191.

The pouch containing the liquid is then sealed in a sealing area within the peelable area, near the top of the passage and substantially transversely to its axis.

After filling, the pouch is welded to close it. For example, a welding electrode (for thermal welding or thermal pulse welding) melts the sealing and peelable material and so seals the pouch. Note that this sealing is more akin to gluing than welding since only the sealing material is melted and not the thermoplastics material film. The thermoplastics material films adhere to each other in the closure area by virtue of the sealing material, which acts as a binder.

The sealing area preferably has a triangular cross-section. The base of the triangle and the sealing area then provide high mechanical strength and therefore a good seal. The apex of the triangle enables the application of a progressive opening force, so that the pouch can easily be "peeled open".

The sealing area can also with advantage have an inverted V-shape cross-section. This shape avoids the concentration of stresses in the corners and enables sufficiently strong welds to be formed by the pulsed welding technique.

The present invention allows the pouch to be opened in the required area, i.e. the area delimited by the peelable area and the shape of the welding electrode, by manual separation of the two thermoplastics material films.

Another advantage of the present invention is that the operator does not have to cut or tear the thermoplastics material film with the result that the passage forms a good guide for the insertion of a probe, a tube, a catheter, a syringe, the tip of an insemination gun, etc.

The pouch of the invention can contain any liquid substance that is chemically and biologically compatible with the thermoplastics material film used.

In one particularly advantageous embodiment of the invention the pouch contains a liquid usable for artificial insemination, for example animal semen, a medium or a diluting agent.

The present invention will now be described in more detail with reference to the accompanying drawings, showing a pouch suitable for packaging doses of liquid for artificial insemination.

DETAILED DESCRIPTION OF THE PREFERRED EMBODIMENTS

Figure 1:
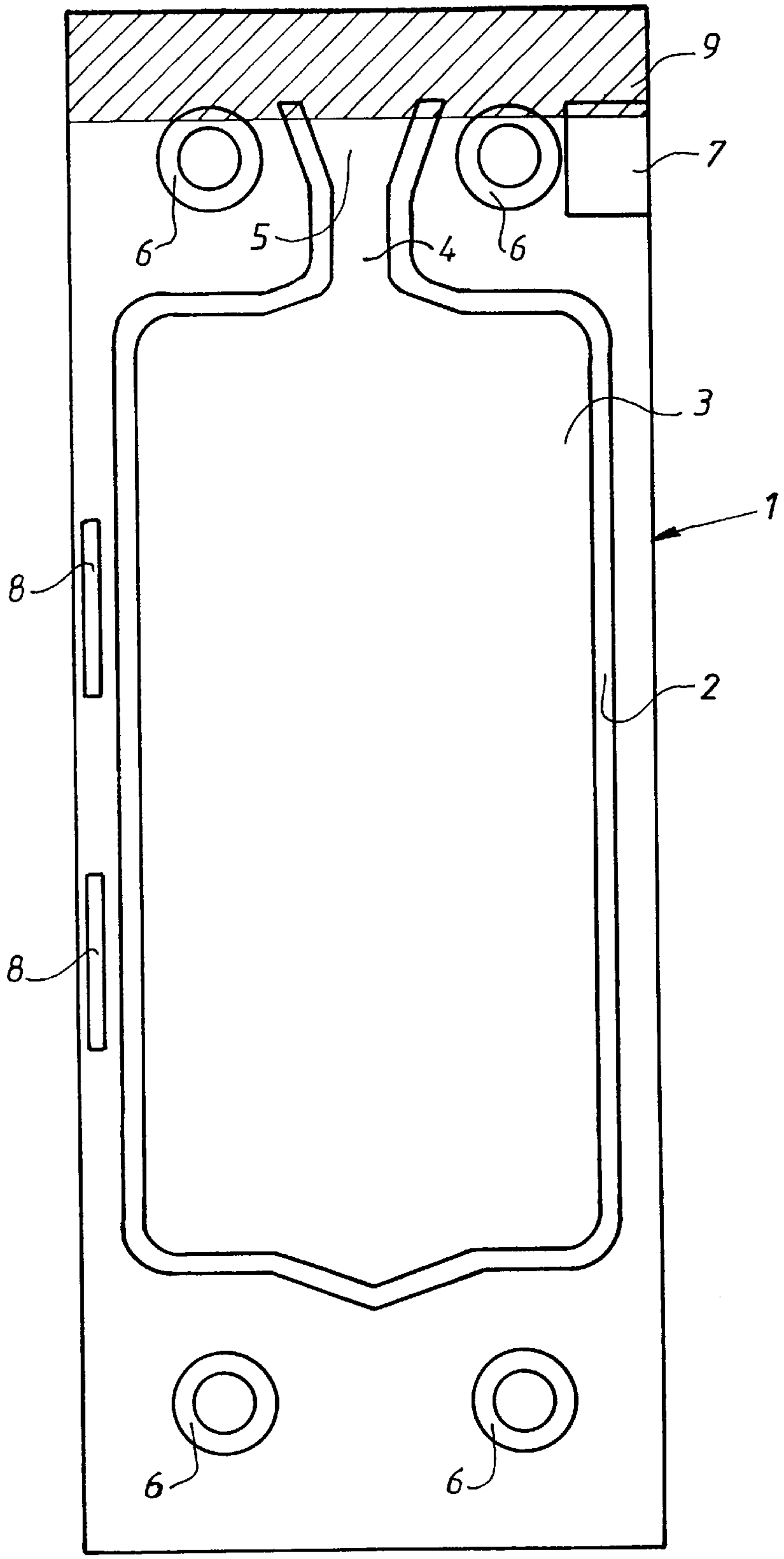
FIG. 1 is a cross-sectional view of an unsealed pouch extracted from a strip of pouches.

The pouches 1 are designed to be fed through a packaging machine in the form of a strip comprising a succession of pockets along the strip which is rolled up for storage.

The pouch 1, made of two welded thermoplastics material films, is substantially rectangular in shape when empty, the weld 2 delimiting a pocket 3 having the required shape of the pouch. The pocket 3 is extended at the top by a passage 4 extended by an insertion and centering flare or cone 5.

Substantially equidistant holes 6 are formed near two longitudinal edges of the strip, outside the weld. These holes are used to feed the thermoplastics material strip through a packaging machine and to support it therein.

Welding areas 7 and 8 are provided to hold the two thermoplastics material films together and prevent them separating in the feed device of the packaging machine.

At least one of the two thermoplastics material films has a peelable area 9 at the top which is obtained by depositing a sealing and peelable material such as wax, for example.

Figure 2:
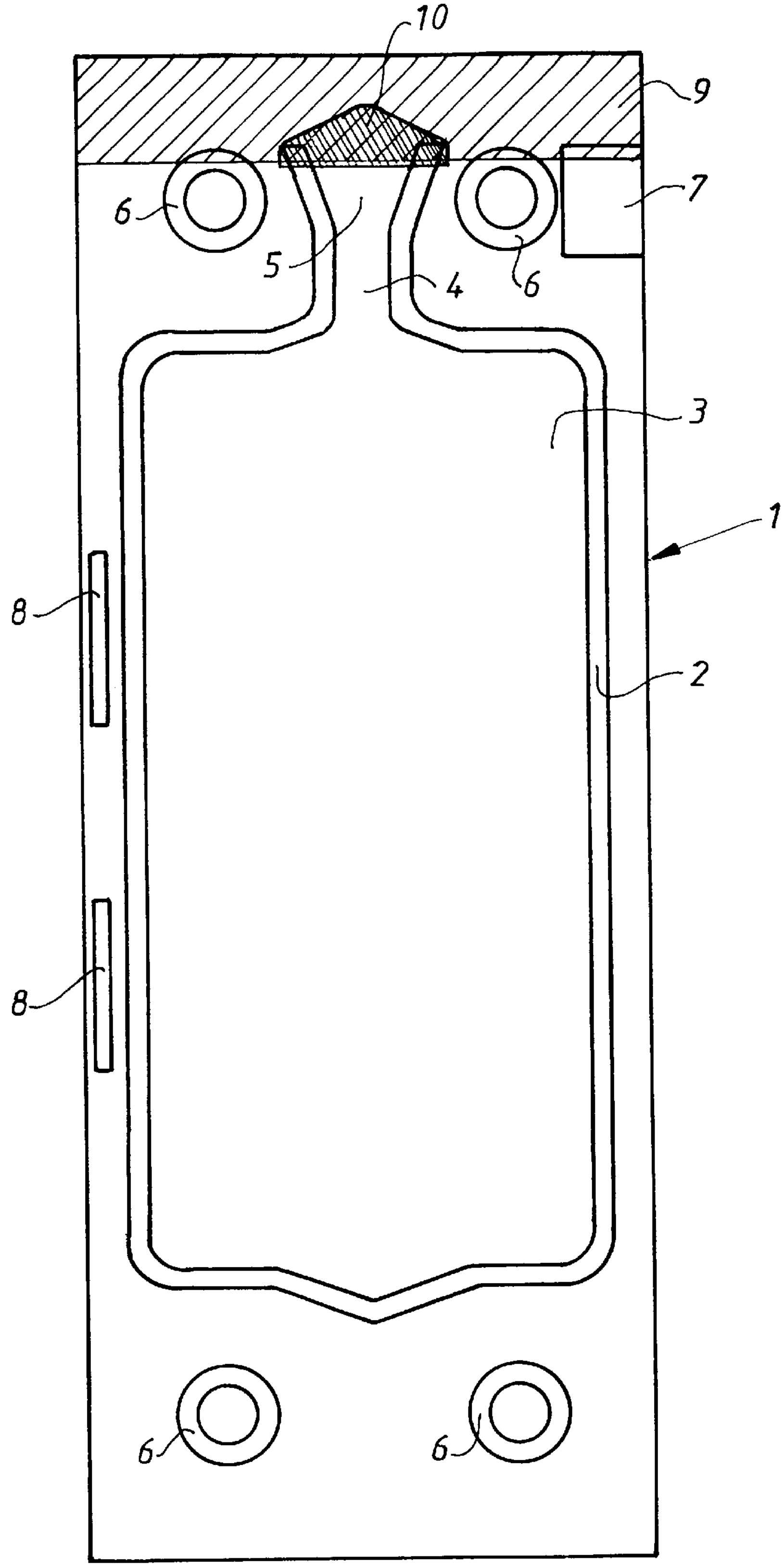
FIG. 2 is a cross-sectional view of a sealed pouch.
Figure 3:
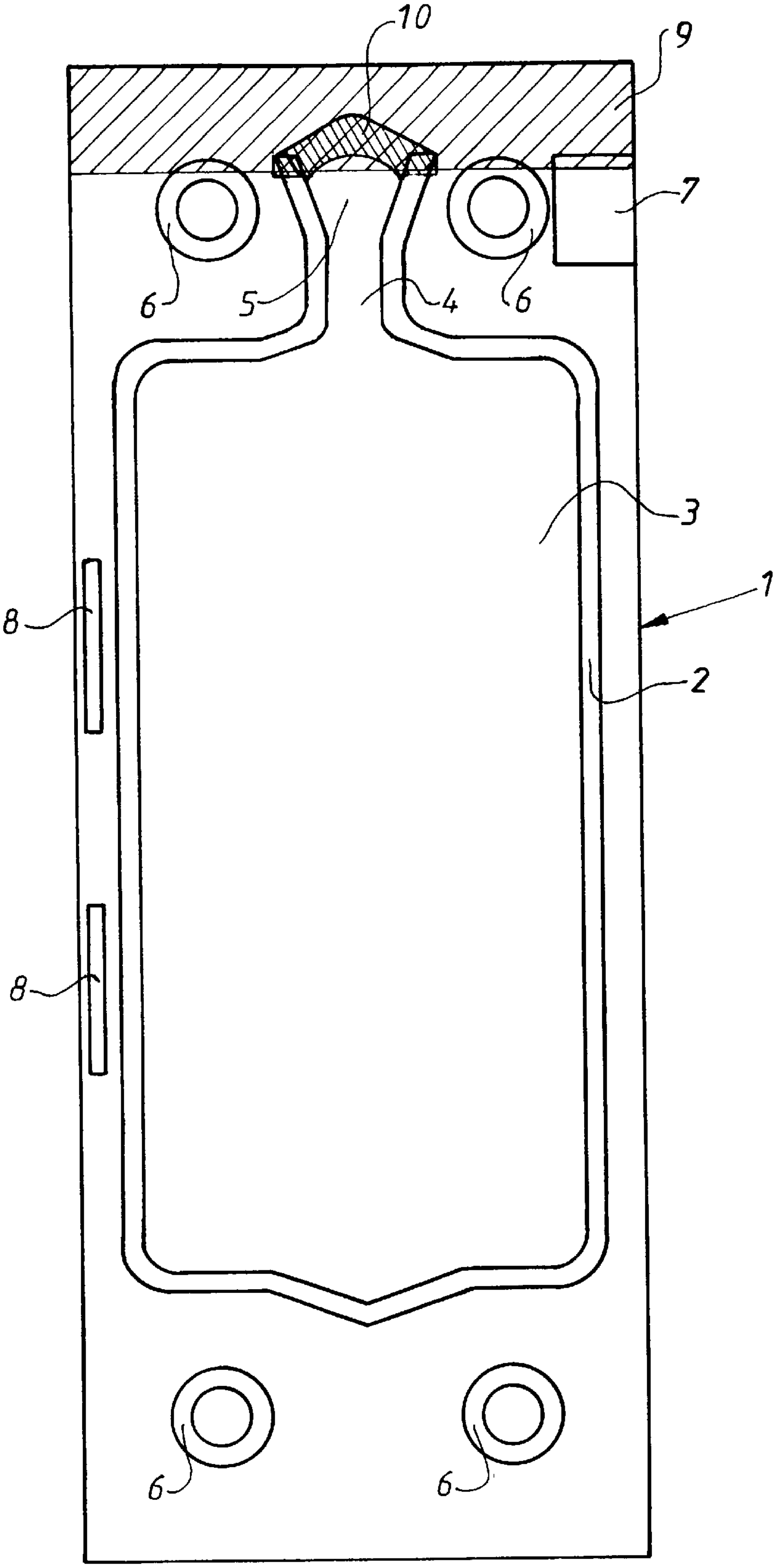
FIG. 3 is a cross-sectional view of a sealed pouch with a variant shape of the sealing area.

When the pouch is closed, after filling, the sealing and peelable material is melted locally in the sealing area 10. The cross-section of the sealing area 10 is triangular in FIG. 2 and of inverted V-shape in FIG. 3.

To open the pouch, the operator separates the two thermoplastics material films manually. The pouch can thus be opened easily in the required area, i.e. the area delimited by the peelable area and the shape of the welding electrodes. A probe or a tube can then be inserted into the opening, which provides positive guidance.

Although the invention has been described and shown with particular reference to the specific field of artificial insemination of animals, it is to be understood that the skilled person will be able to conceive numerous variants that do not depart from the scope of the invention. Moreover, although the invention has considerable advantages in the field of packaging liquids for artificial insemination of animals, the liquid substances that can be packaged in the pouch of the invention are not limited to the veterinary field but can belong to the field of human medicine.

There is claimed:

1. A pouch or sachet for packaging biologic liquid substances comprising two thermoplastic material films welded together by a weld delimiting a pocket and a filler passage connected to the top of the pocket, one of said two thermoplastic material films having a peelable area at the top of said pocket and the peelable area containing a sealing and peelable material separate from and between the two thermoplastic material films in a closure area of the peelable area, said filler passage providing an inlet and outlet to said pocket when said peelable area is opened, said sealing and peelable material capable of being melted to adhere the two thermoplastic material films together in said closure area without melting the two thermoplastic material films, said peelable area capable of being opened without degrading the integrity of the two thermoplastic films, and the peelable material capable of being remelted to reclose the peelable area without melting the two thermoplastic material films.

2. The couch claimed in claim 1 wherein said two thermoplastic material films adhere to each other in said closure area by said sealing and peelable material, which acts as a binder.

3. The pouch claimed in claim 2 wherein said sealing and peelable material is wax.

4. The pouch claimed in claim 1 wherein said filler passage is extended by a flare.

5. The pouch claimed in claim 1 wherein said two thermoplastic material films are offset relative to each other at the top of said pocket.

6. The pouch claimed in claim 5 wherein said offset is of approximately 2 mm to 3 mm.

7. In combination, a pouch as defined in claim 1 and a biologic liquid substance contained in the pocket, the pocket being sealed in a sealing area within said peelable area near the top of said passage and substantially transversely to the axis of the passage.

8. The pouch claimed in claim 7 wherein said sealing area has a triangular cross-section.

9. The pouch claimed in claim 7 wherein said sealing area has an inverted V-shape cross-section.

10. The pouch claimed in claim 1 wherein said biologic liquid substance is for artificial insemination.

11. The pouch claimed in claim 10 wherein said biologic liquid substance for artificial insemination is selected from animal semen, media and diluting agents.

* * * * *